US00H002191H

(19) United States

(12) Statutory Invention Registration (10) Reg. No.: US H2191 H

Wang (43) Published: Jun. 5, 2007

(54) IDENTIFICATION AND MAPPING OF SINGLE NUCLEOTIDE POLYMORPHISMS IN THE HUMAN GENOME

(75) Inventor: David G. Wang, Lake Zurich, IL (US)

(73) Assignee: SNP Consortium, Chicago, IL (US)

(21) Appl. No.: 09/925,065

(22) Filed: Aug. 8, 2001

(65) Prior Publication Data

US 2004/0181048 A1 Sep. 16, 2004
US 2005/0228172 A9 Sep. 16, 2004

Related U.S. Application Data

(60) Provisional application No. 60/243,096, filed on Oct. 24, 2000, provisional application No. 60/252,147, filed on Nov. 20, 2000, provisional application No. 60/250,092, filed on Nov. 30, 2000, provisional application No. 60/261,766, filed on Jan. 16, 2001, and provisional application No. 60/289,846, filed on May 9, 2001.

(51) Int. Cl.
*C12Q 1/68* (2006.01)

(52) U.S. Cl. ..... 435/6; 536/24.33; 536/24.3; 536/23.1

(58) Field of Classification Search ..... 536/24.33, 536/24.3, 23.1; 435/6
See application file for complete search history.

(56) References Cited

U.S. PATENT DOCUMENTS 5,474,796 A * 12/1995 Brennan ..... 427/2.13

OTHER PUBLICATIONS

Otterness et al. (Clin. Pharmacol. Ther, 1997; 62:60–73).*

GenBank AB045146 (GI: 8777468, Aug. 22, 2000).*

* cited by examiner

*Primary Examiner*—M. Clement
(74) *Attorney, Agent, or Firm*—Wilmer Cutler Pickering Hale and Dorr LLP

(57) ABSTRACT

The invention relates to the role of genes in human diseases. More particularly, the invention relates to compositions and methods for identifying genes that are involved in human disease conditions. The invention provides identification and mapping of a very large number of SNPs throughout the entire human genome. This contribution allows scientists to isolate and identify genes that are relevant to the prevention, causation, or treatment of human disease conditions.

1 Claim, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

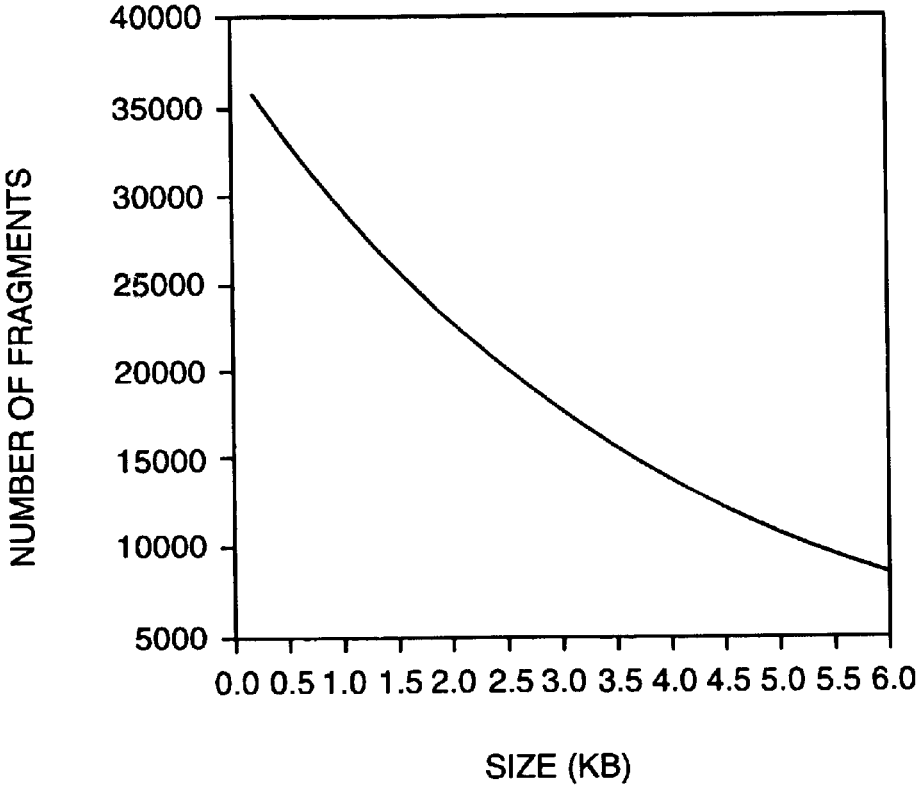
40000
35000
30000
25000
20000
15000
10000
5000
NUMBER OF FRAGMENTS
0.0 0.5 1.0 1.5 2.0 2.5 3.0 3.5 4.0 4.5 5.0 5.5 6.0
SIZE (KB)

IDENTIFICATION AND MAPPING OF SINGLE NUCLEOTIDE POLYMORPHISMS IN THE HUMAN GENOME

CROSS REFERENCE TO RELATED APPLICATIONS

This application claims priority to the following provisional applications: U.S. patent application Ser. No. 60/243,096, Oct. 24, 2000; U.S. patent application Ser. No. 60/252,147, Nov. 20, 2000; U.S. patent application Ser. No. 60/250,092, Nov. 30, 2000; U.S. patent application Ser. No. 60/261,766, Jan. 16, 2001; and U.S. patent application Ser. No. 60/289,846, May 9, 2001.

BACKGROUND OF THE INVENTION

The Sequence Listing portion of this application is contained on a compact disk (CD), which is incorporated by reference herein in its entirety. The compact disk labled "Sequence Listing Part" contains file "108827-135.zip," 193,477 KB in length, created on Sep. 17, 2003, which is the compressed file "108827-135.st25," 820,249,461 KB in length.

FIELD OF THE INVENTION

The invention relates to the role of genes in human diseases. More particularly, the invention relates to compositions and methods for identifying genes that are involved in human disease conditions.

SUMMARY OF THE RELATED ART

During the past two decades, remarkable developments in molecular biology and genetics have produced a revolutionary growth in understanding of the implication of genes in human disease. Genes have been shown to be directly causative of certain disease states. For example, it has long been known that sickle cell anemia is caused by a single mutation in the human beta globin gene. In many other cases, genes play a role together with environmental factors and/or other genes to either cause disease or increase susceptibility to disease. Prominent examples of such conditions include the role of DNA sequence variation in ApoE in Alzheimer's disease, CKR5 in susceptibility to infection by HIV; Factor V in risk of deep venous thrombosis; MTHFR in cardiovascular disease and neural tube defects; p53 in HPV infection; various cytochrome p450s in drug metabolism; and HLA in autoimmune disease.

Surprisingly, the genetic variations that lead to gene involvement in human disease are relatively small. Approximately 1% of the DNA bases which comprise the human genome contain polymorphisms that vary at least 1% of the time in the human population. The genomes of all organisms, including humans, undergo spontaneous mutation in the course of their continuing evolution. The majority of such mutations create polymorphisms, thus the mutated sequence and the initial sequence co-exist in the species population. However, the majority of DNA base differences are functionally inconsequential in that they neither affect the amino acid sequence of encoded proteins nor the expression levels of the encoded proteins. Some polymorphisms that lie within genes or their promoters do have a phenotypic effect and it is this small proportion of the genome's variation that accounts for the genetic component of all difference between individuals, e.g., physical appearance, disease susceptibility, disease resistance, and responsiveness to drug treatments.

The relation between human genetic variability and human phenotype is a central theme in modern human genetic studies. The human genome comprises approximately 4 billion bases of DNA. The Human Genome Project is uncovering more and more of the of the consensus sequence of this genome. However, there remains a need to identify the nature and location of genetic variations that are implicated in human disease conditions.

Sequence variation in the human genome consists primarily of single nucleotide polymorphisms ("SNPs") with the remainder of the sequence variations being short tandem repeats (including microsatellites), long tandem repeats (minisatellite) and other insertions and deletions. A SNP is a position at which two alternative bases occur at appreciable frequency (i.e. >1%) in the human population. A SNP is said to be "allelic" in that due to the existence of the polymorphism, some members of a species may have the unmutated sequence (i.e., the original "allele") whereas other members may have a mutated sequence (i.e., the variant or mutant allele). In the simplest case, only one mutated sequence may exist, and the polymorphism is said to be diallelic. The occurrence of alternative mutations can give rise to triallelic polymorphisms, etc. SNPs are widespread throughout the genome and SNPs that alter the function of a gene may be direct contributors to phenotypic variation. Due to their prevalence and widespread nature, SNPs have potential to be important tools for locating genes that are involved in human disease conditions. Wang et al., Science 280: 1077–1082 (1998), discloses a pilot study in which 2,227 SNPs were mapped over a 2.3 megabase region of DNA.

To be useful for locating and identifying genetic variations linked to human disease, however, it is necessary to identify and map a much larger number of SNPs, and to do so throughout the human genome. There is therefore a need for the identification and mapping of a very large number of SNPs throughout the entire human genome.

BRIEF SUMMARY OF THE INVENTION

The invention provides identification and mapping of a very large number of SNPs throughout the entire human genome.

In a first aspect, the invention provides SNP probes which are useful in classifying people according to their genetic variation. The SNP probes according to the invention are oligonucleotides which can discriminate between alleles of a SNP nucleic acid in conventional allelic discrimination assays.

In a second aspect, the invention provides methods for using a large-scale map of SNPs throughout the human genome to isolate and identify genes that are relevant to the prevention, causation, or treatment of human disease conditions. Preferred embodiments of this aspect of the invention include linkage studies in families, linkage disequilibrium in isolated populations, association analysis of patients and controls and loss-of-heterozygosity studies in tumors.

BRIEF DESCRIPTION OF THE DRAWINGS

FIG. 1 depicts the number of human restriction fragments with sizes in a 200 bp range centered on a given point for a typical six-cutter restriction enzyme.

Table II depicts for each SEQ ID NO., the polymorphism within the consensus sequence, the position of the polymorphism in the consensus sequence along with the identity of the polymorphism and frequency of the alleles, and the map location of the identified sequence. For example, for a polymorphism in which "a" is identified 4 times and "t" is identified 2 times within a consensus sequence at position 35 from the 5' end, the text identifying the sequence will read "SEQ ID NO. ###; polymorphism=w; position=35; alleles=a(4)t(2)." In some cases, the polymorphism consists of a single base deletion. In this case, the deleted base is indicated as a hyphen (-). The map location of the listed sequence is described by each of the various means which were used to identify the location, including the following:

1) base location relative to GenBank hit is listed as "sequence=ACC/Off" where "Acc" is the accession number of the matching GenBank entry and "Off" is the offset of the polymorphism from the start of the GenBank entry, for example, "sequence=M39218/98112" indicates that the polymorphism is 98,112 base pairs offset from the start of GenBank entry M39218.
2) chromosome number is listed as chromosome=N, where N is the chromosome number, for example "chromosome=12".
3) cytogenetic position is listed as cytogenetic=I, where I is the cytogenetic position, for example "cytogenetic=1q12.3".
4) radiation hybrid ("rh") position relative to a GenBank entry is listed as rh=Acc/Offset (P), where "Acc" is the accession number of the relative GenBank entry, "Offset" is the centiray distance from the relative Genbank entry, and "(P)" is the radiation hybrid panel used. For example "rh=M39128/21.2 (TNG)" indicates that the sequence is located 21.2 centiray from GenBank entry M39128 using the TNG radiation hybrid panel. Multiple map coordinates may be provided for any SEQ ID NO. and each coordinate is separated by a space, for example "map location=[chromosome=12 rh=M39128/21.2(TNG) cytogenetic-12q18.1]." When the map position is unknown, the map fields are blank.

DETAILED DESCRIPTION OF THE PREFERRED EMBODIMENTS

The invention relates to the role of genes in human diseases. More particularly, the invention relates to compositions and methods for identifying genes that are involved in human disease conditions. Any patents and publications cited herein reflect the knowledge in this field and are hereby incorporated by reference in entirety. Any conflict between any reference cited herein and the specific teachings of this specification shall be resolved in favor of the latter.

The invention provides identification and mapping of a very large number of SNPs throughout the entire human genome. This contribution allows scientists to isolate and identify genes that are relevant to the prevention, causation, or treatment of human disease conditions.

In a first aspect, the invention provides SNP probes which are useful in classifying people according to their genetic variation. The SNP probes according to the invention are oligonucleotides which can discriminate between alleles of a SNP nucleic acid in conventional allelic discrimination assays. As used herein, a "SNP nucleic acid" is a nucleic acid sequence which comprises a nucleotide which is variable within an otherwise identical nucleotide sequence between individuals or groups of individuals, thus existing as alleles. Such SNP nucleic acids are preferably from about 15 to about 500 nucleotides in length. The SNP nucleic acids may be part of a chromosome, or they may be an exact copy of a part of a chromosome, e.g., by amplification of such a part of a chromosome through PCR or through cloning.

The SNP probes according to the invention are oligonucleotides that are complementary to a SNP nucleic acid. The term "complementary" means exactly complementary throughout the length of the oligonucleotide in the Watson and Crick sense of the word. In certain preferred embodiments, the oligonucleotides according to this aspect of the invention are complementary to one allele of the SNP nucleic acid, but not to any other allele of the SNP nucleic acid. Oligonucleotides according to this embodiment of the invention can discriminate between alleles of the SNP nucleic acid in various ways. For example, under stringent hybridization conditions, an oligonucleotide of appropriate length will hybridize to one allele of the SNP nucleic acid, but not to any other allele of the SNP nucleic acid. (See e.g., Saiki et al., Proc. Natl. Acad. Sci. USA 86: 6230–6234 (1989)). For this application, preferred oligonucleotide lengths are from about 15 nucleotides to about 25 nucleotides. Preferred final hybridization conditions for this application are 2× PBS at room temperature. Preferably, the oligonucleotide is labeled, most preferably by a radiolabel, an enzymatic label, or a fluorescent label. Alternatively, an oligonucleotide of appropriate length can be used as a primer for PCR, wherein the 3' terminal nucleotide is complementary to one allele of the SNP nucleic acid, but not to any other allele. In this embodiment, the presence or absence of amplification by PCR determines the haplotype of the SNP nucleic acid.

To identify the SNP nucleic acids (sometimes referred to hereafter simply as "SNPs") present in the human genome, a whole genome approach was taken to identify SNPs on a large scale. The method described in the following examples, termed the "Reduced-Representation Shotgun" or "RRS", was utilized as it allows the random sequencing of a specific subset (e.g., 1%) of the genome from a collection of individuals.

Our intent was to sequence each fraction of the genomic DNA to a depth of 2.5–5× coverage. This level of coverage was determined through a calculation of Poisson sampling for different levels of SNP allele frequency. Briefly, the proportion of SNPs identified increases with the depth of coverage of the sequencing (the sequencing of a fragment from one individual provides 1× of coverage and the sequencing of the same fragment from each additional individual provides and additional 1× of coverage), and more common SNPs are more rapidly detected than less common SNPs. The efficiency of detection, or number of SNPs detected per additional 1× depth of coverage, however, peaks at about 2.5× coverage and diminishes significantly when greater than 5× coverage is obtained (calculation not shown).

The distribution of restriction sites tends to be uniform across the human genome (with the exception of restriction sites containing the CpG dinucleotide). Thus, the proportion of the genome present in any size fraction can be varied by the size and extent of the fraction taken. For example, in a survey of available genomic sequence data on chromosomes 22 and X, the frequency and distribution of restriction fragments was examined, see Table 1.

TABLE 1

Distribution of Restriction Fragments in Genomic Sequence.

| Enzyme | EcoRI | EcoRV | BamHI | HindIII | HindIII |
|---|---|---|---|---|---|
| Chromosome | 22 | 22 | 22 | 22 | X |

TABLE 1-continued

Distribution of Restriction Fragments in Genomic Sequence.

| Enzyme | EcoRI | EcoRV | BamHI | HindIII | HindIII |
|---|---|---|---|---|---|
| Size Range (kb) | | | | | |
| 1–2 | 40.9 | 13.7 | 29.7 | 44.6 | 67.5 |
| 2–3 | 33 | 12.6 | 24.8 | 32.7 | 46.6 |
| 3–4 | 27 | 9.4 | 18.5 | 26.2 | 34.5 |
| 4–5 | 17.3 | 9.5 | 15 | 20.9 | 23.8 |
| 5–7 | 28.3 | 15 | 22.1 | 25.8 | 29.3 |
| 7–9 | 16.2 | 8.7 | 15.4 | 16 | 15.6 |
| 9–11 | 10 | 9.1 | 11.9 | 8.5 | 8.6 |

(Values are given as number of fragments per Mb, calculated from analysis if 14 Mb or 22 Mb of genomic sequence on chromosomes 22 or X, respectively)

Chromosome-specific variation of restriction site distribution is illustrated by a comparison of the HindIII analysis for chromosomes 22 and X. For this reason, RRS plasmid libraries made using different restriction enzymes are quite useful. The results of restriction fragment distribution shown in Table I above indicate that for the approximately 50 Mb of chromosome 22, about 850 distinct fragments will theoretically be present in a 2–2.5 kb fraction of HindIII or EcoRI fragments, and a 5× coverage of the sequence of both ends of these fragments requires approximately 11,000 reads. In practice about 25% more reads were taken as each fraction contains some spillover of fragments from adjacent size fractions.

The number of restriction sites in the entire human genome for a typical six-cutter restriction enzyme can be calculated and plotted as shown in FIG. 1. As shown in FIG. 1, there are roughly 33,000 fragments in the range of 400–600 bp, and about 22,000 fragments in the range 1.9–2.1 kb. Each 400–600 bp fragment could be sequenced in a single sequencing reaction, and each 1.9–2.1 kb fragment could be sequenced in two sequencing reactions, one from each end. Thus it is apparent that approximately 33,000 reads of fragment in the range 400–600 bp or 44,000 sequencing reads would each provide 1× coverage of the SNPs present in the selected fraction of the human genome.

The oligonucleotides according to this aspect of the invention are useful for identifying people according to their haplotype for a panel of SNP nucleic acids. This can be achieved by obtaining a nucleic acid sample from an individual and using the oligonucleotides according to the invention to assay for which allele the individual has for a particular set of SNP nucleic acids disclosed herein, as discussed above. If a sufficiently large number of SNP nucleic acids are assayed, a unique haplotype can be established as a reference for that individual. Subsequently, if a biological sample which may be from that individual needs to be identified, e.g., for forensic purposes, the oligonucleotides according to the invention can be used in identical assays on the biological sample, and the results can be compared to the reference haplotype to determine whether the biological sample is from the same individual. The oligonucleotides according to the invention are also useful in studies to determine the relevance of various genes to the prevention, causation or treatment of various human disease conditions, as further discussed below.

Thus, in a second aspect, the invention provides methods for using a large-scale map of SNPs throughout the human genome to isolate and identify genes that are relevant to the prevention, causation, or treatment of human disease conditions. Preferred embodiments of this aspect of the invention include linkage studies in families, linkage disequilibrium in isolated population, association analysis of patients and controls and loss-of-heterozygosity studies in tumors.

The SNP map and its methods of use according to this aspect of the invention transform the search for susceptibility genes through the use of association studies and through the use of linkage disequilibrium studies. Linkage disequilibrium studies are indirect studies in which an investigator seeks to identify the presence of common ancestral chromosomes among susceptible individuals. Association studies are direct studies in which an investigator tests whether a genetic variant increases disease risk by comparing allele frequencies in affecteds and controls. Association studies make possible the identification of genes with relatively common variants that confer a modest or small effect on disease risk, which is precisely the type of gene expected in the most complex disorders. Association studies are logistically simpler to organize and are potentially more powerful than family-based linkage studies, but they have previously had the practical limitation that one can only test a few guesses rather than being able to systematically scan the entire genome. In the method according to the invention, association studies can be extended to include a systematic search through the entire list of common variants in the human genome to reveal the identity of the gene or genes underlying any phenotype not due to a rare allele. The SNP map of the human genome provided by the invention will make it possible to test disease susceptibility against every common variant simultaneously, for example, by genotyping a well-characterized clinical population with a comprehensive DNA array.

The SNP map used in this aspect of the invention can be prepared using a variety of methods. One traditional method of mapping the locus of a SNP is to create a PCR assay to amplify the locus and then to perform genetic mapping or whole-genome radiation hybrid ("RH") mapping. Another method for mapping the locus of a SNP is "in silico mapping" in which the SNP and its flanking sequence is "BLASTed" against the publicly available sequence, such as the sequence managed by NCBI or GenBank, in order to identify the genomic overlaps that will positionally map the SNPs. We utilized both RH mapping and in silico mapping to map the locus of the SNPs.

The location of the identified SNPs was mapped by RH mapping onto the existing Stanford TNG panel through developing each SNP as an STS. The TNG panel was chosen for mapping as it has been shown to order new STS's with greater than 95% confidence at 100 kb resolution. The Stanford TNG panel consists of 90 independent hybrids with an average human marker retention per hybrid of 19%. This panel was constructed with 50,000 rad of irradiation, resulting in human chromosomal fragments 300 kb average size. The practical resolution of the TNG panel is 21 kb. One can think of the TNG panel as a "clone library", representing a 17-fold redundancy of the human genome, with a human insert size of 300 kb and 333,000 detectable ends.

This map can be used for conventional linkage studies in families, linkage disequilibrium studies in isolated population, association analysis of patients and controls and loss-of-heterozygosity studies in tumors. For example, the linkage disequilibrium method of Hastbacka et al., Nature Genetics 2: 204–211 (1992), can be used, substituting SNPs according to the invention for the RFLPs used in that report. Briefly, linkage disequilibrium mapping is based on the observation that chromosomes having a gene associated with disease which are descended from a common ancestral mutation should show a distinctive haplotype in the immediate vicinity of the gene, reflecting the haplotype of the ancestral chromosome. For example, the method is particularly useful when there is a single disease-causing allele with a high frequency, so that the excess of an ancestral haplotype can be detected easily, and when the allele was introduced into the population sufficiently long ago that recombination has made the region of strongest linkage relatively small. Population genetics are then used to determine how much recombination should be expected between the gene and one or more nearby SNPs of known map location, thus locating the gene with respect to the SNP map.

The following examples are intended to further illustrate certain preferred embodiments of the invention, and are not intended to be limiting in nature.

EXAMPLE 1

Cloning and Identification of SNP Nucleic Acids

Genomic DNA was isolated from a plurality of unrelated human individuals and approximately equal amounts from each individual was pooled. The combined genomic DNA was then cut to completion with one of the following restriction enzymes: HindIII, EcoRI, EcoRV, and BamHI. Other restriction enzymes are also useful. The digested genomic DNA was then run on a preparative agarose gel along with size markers. The agarose gel containing the electrophoresed DNA was cut into size fractions such that a size range of about 200 base pairs was present in each slice (e.g., 500–700 base pairs, 1000–1200 base pairs, 2200–2400 base pairs). The DNA was extracted from the gel. Eluted size fractionated DNA fragments were ligated into a phosphatased vector which had been cut using the same restriction enzyme as was used for the digestion of the genomic DNA. Plasmid libraries were prepared by transforming *E. coli* with the ligated vectors according to well known methods of transformation. The plasmid libraries were tested to confirm that they contained a high proportion of inserts in the selected size fractionation range.

Random colonies of the transformed bacteria were picked for sequencing from one or both ends of the genomic DNA insert. Any available method of DNA sequencing could be utilized, and dye terminator chemistry was preferred for its optimum resolution of the heterozygotes. As the genomic DNA libraries were made from a pool of individuals and the DNA was size fractionated prior to preparation of the DNA library, each fragment in the library was sampled multiple times, but in almost every case each sequencing read from a given fragment is derived from a different DNA sample thus providing a depth of coverage of the DNA genomic sequences which otherwise would be unattainable.

After sequencing of the fragments, the sequences were clustered after masking all known repeats. The sequences can be clustered using readily available sequence assembly programs, e.g. Phrap. The sequences of each cluster were compared and inspected for base differences, and candidate SNPs were identified at positions where each base was represented by a Phred quality score of >20. All sequence variants other than SNPs, an estimated 20–25% of the total, were also noted. All SNPs, and other variants, which occurred in repetitive sequences were discarded and the remainder were entered into a candidate SNP database.

A subset of the candidate SNPs were verified to confirm that the majority of the candidate SNPs identified by sequence analysis were informative. The verification was done using a PCR assay to amplify DNA from several individuals, plus a few pools of genomic DNA from distinct ethnic groups and the PCR products were sequenced using dye terminator chemistry for optimum detection of heterozygotes. The results, not shown, of the small-scale verification indicated that the identified SNPs were informative.

In this manner we were able to identify the SNPs contained within the specific subset of DNA which was sequenced. Through reiterative use of the RRS method, we were able to identify the majority of the SNPs present in the human genome. The identified SNPs are listed in Table II.

EXAMPLE 2

Generation of SNP Maps

Each SNP was developed into an STS and mapped using the TNG panel by using the method of Stewart et al. (1997) Genome Research, vol. 7, pp. 422–433. Briefly, oligonucleotides for PCR amplification of the fragments containing the SNPs were chosen using PRIMER 3.0, a software package written at the Whitehead Genome Center. The oligonucleotide primers were chosen according to parameters that generate PCR products of 100–400 base pairs in length and that allow the use of a single set of PCR conditions for all STSs. PCR products are assayed by ethidium bromide staining following agarose gel electrophoresis. An STS containing an identified SNP is judged successful when the primers produce a distinct PCR product of the expected size from total human DNA, but fails to produce a distinct PCR product of this size from hamster genomic DNA. In addition, each successful STS is PCR amplified on a set of approximately 90 rodent-human somatic cell hybrids to assure that the STS maps to a unique human chromosome. Ethidium stained gel images were captured using a CCD camera system and captured data was automatically entered into our mapping database.

The map location for each identified SNP is listed with the SNP sequence in Table II.

EXAMPLE 3

SNP Profiling to Identify an Individual

Oligonucleotides that recognize one allele of a SNP nucleic acid are immobilized on a filter. Preferably, the oligonucleotides comprise oligonucleotides complementary to at least 10 different SNP nucleic acids and are present on the filter in a pre-arranged array. Each filter with bound oligonucleotides is placed in 4 ml hybridization solution containing 5× SSPE, 0.5% $NaDodSO_4$ and 400 ng of streptavidin-horseradish peroxidase conjugate (SeeQuence; Eastman Kodak). PCR-amplified DNA made with biotinylated primers (20 microliters) from a sample of blood from an individual is denatured by addition of an equal volume of 400 mM NaOH/10 mM EDTA and added immediately to the hybridization solution, which is then incubated at 55° C. for 30 minutes. The filters are briefly rinsed twice in 2× SSPE, 0.1% $NaDodSO_4$ at room temperature, washed once in 2× SSPE, 0.5% $NaDodSO_4$ at 55° C. and then briefly rinsed twice in 2× PBS (1× PBS is 137 mM NaCl/2,7 mM KCl/8 mM $Na_2HPO_4$/1.5 mM $KH_2PO_4$, pH 7.4) at room temperature. Color development is performed by incubating the filters in 25–50 ml red leuco dye (Eastman Kodak) at room temperature for 5–10 minutes. The result is photographically recorded and the pattern can subsequently be compared with another biological sample to determine whether the individual can be excluded as the source of the biological sample.

EXAMPLE 4

Analysis of Clipped Reads

All RRS reads were clipped of sequencing vector and low quality ends, which set a usable read length for each read.

The clipped reads were screened for repetitive sequence with RepeatMasker, using the default human settings. Only reads with >=80 non-repetitive bases and >=100 Phred quality (Q)>=30 bases were used in this analysis. These RRS reads were assembled using phrap_manyreads. Contigs with 2 or more reads must be aligned from a common starting point, the enzyme identified in the Production Protocol. High quality base discrepancies, Q>=23, were identified as candidate SNPs. Further restrictions on the candidate SNPs were that its neighbouring 5 bases all had Q>=15, and that at least 9 of these 10 neighbouring bases agreed with the consensus. If the number of detected SNPs in one clique was greater than 4 or the depth of the assembly (not including the genomic sequence) was greater than 5, then all SNPs were discarded for that contig.

EXAMPLE 5

PCR Confirmation of Polymorphism

PCR primers were designed to flank each candidate SNP, and the resulting fragment amplified from each of the DNAs used to construct the library. SNPs were considered validated if at least two distinct genotypes were observed at the candidate position (or three, if a homozygous variant was observed); in addition, no position could be heterozygous in all individuals, as this would indicate a repeat sequence.

EXAMPLE 6

BLAST Analysis/Comparison of Base Call and Quality

Each sequence was blasted to a library of known repeat sequences, and any read containing >50% of bases in repeats was removed. The remaining reads were blasted against one another, and candidate pairs identified if they shared >80% sequence identity over at least 270 bases. These candidate pairs were aligned using a modified Smith-Waterman alignment, and candidate SNPs identified (see below). Two filters were used to ensure high accuracy of declaring a sequence match, and to avoid inclusion of low-level repeat sequences. First, a pair was declared only if the sequences aligned over their entire length (save 50 bp allowed on either end for sequencing end-effects), and no more than 1% of the bases in the alignment were candidate SNPs (see below). Second, pairs were then arranged into higher-order connected component groups (using transitivity). Component groups with more than 8 reads were removed. Paired sequences (see above) were run through the algorithm "SNPfinder", which compares the base-call and quality of each position. A candidate SNP was declared if two basecalls were present, the Phred score of each was >20, and the 10 bases flanking the SNP (5 on either side) were of Phred quality >15.

EXAMPLE 7

Cloning and Sequencing to Confirm Polymorphism

A pool of 10 DNAs (the Pilot Panel) or 24 DNAs (the TSC Panel) was digested with a restriction enzyme, size fractionated on an agarose gel, and cloned into M13-based vectors. Sequences were obtained on ABI 377 or 3700 sequencers.

Base-calling was performed with Phrap.

What is claimed is:

1. A SNP probe consisting of an oligonucleotide that is complementary to a SNP nucleic acid selected from the SNP nucleic acids shown in SEQ ID NOs: 1–12,108.

* * * * *

UNITED STATES PATENT AND TRADEMARK OFFICE

CERTIFICATE OF CORRECTION

REGISTRATION NO. : US H2191 H
APPLICATION NO. : 09/925065
DATED : June 5, 2007
INVENTOR(S) : David G. Wang It is certified that error appears in the above-identified patent and that said Letters Patent is hereby corrected as shown below:

In the Specification:

In Columns 9 and 10, immediately before the claims, please insert the following page-wide SEQUENCE LISTING statement:

--

---

SEQUENCE LISTING

The statutory invention registration contains a lengthy "Sequence Listing" section. A copy of the "Sequence Listing" is available in electronic form at the USPTO web (http://seqdata.uspto.gov/?pageRequest=docDetail&DocID=USH0002191H1). An electronic copy of the "Sequence Listing" will also be available from the USPTO upon request and payment of the fee set forth in 37 CFR 1.19(b)(3).

---

--

Signed and Sealed this

Twenty-first Day of September, 2010

David J. Kappos

David J. Kappos
*Director of the United States Patent and Trademark Office*